(12) United States Patent
Caruel et al.

(10) Patent No.: US 10,506,808 B2
(45) Date of Patent: Dec. 17, 2019

(54) COMPOSITION AND RODENTICIDE BAIT COMPRISING DIFETHIALONE AND METHOD FOR CONTROLLING TARGET RODENT PESTS

(71) Applicants: LIPHATECH, Pont-du-Casse (FR); INSTITUT ENSEIGENMENT SUPERIEUR ET RECHERCHE EN ALMENTATION SANTE ANIMALE SCIENCES AGRONOMIQUES ET ENVIRONNEMENT (VET AGRO SUP), Marcy l'Etoile (FR)

(72) Inventors: Herve Caruel, Moncaut (FR); Etienne Benoit, Lyons (FR); Isabelle Fourel, Miribel (FR); Virginie Lattard, Lyons (FR)

(73) Assignees: LIPHATECH, Pont-du-Casse (FR); Institut Enseigenment Superieur Et Recherche En Alme, Marcy l'Etoile (FR)

( * ) Notice: Subject to any disclaimer, the term of this patent is extended or adjusted under 35 U.S.C. 154(b) by 0 days.

(21) Appl. No.: 15/735,677

(22) PCT Filed: Dec. 6, 2016

(86) PCT No.: PCT/EP2016/079859
§ 371 (c)(1),
(2) Date: Dec. 12, 2017

(87) PCT Pub. No.: WO2017/097748
PCT Pub. Date: Jun. 15, 2017

(65) Prior Publication Data
US 2018/0360038 A1    Dec. 20, 2018

(30) Foreign Application Priority Data

Dec. 11, 2015 (FR) .................................... 15 62236

(51) Int. Cl.
*A01N 43/18* (2006.01)
*A01N 25/00* (2006.01)

(52) U.S. Cl.
CPC ........... *A01N 43/18* (2013.01); *A01N 25/004* (2013.01)

(58) Field of Classification Search
CPC .............................. A01N 43/18; A01N 25/004
See application file for complete search history.

(56) References Cited

U.S. PATENT DOCUMENTS

| | | | |
|---|---|---|---|
| 2005/0181003 A1 | 8/2005 | Endepols et al. | |
| 2008/0260683 A1* | 10/2008 | Bowman | A01N 25/004 424/84 |
| 2010/0278890 A1* | 11/2010 | Winowiski | A01N 25/04 424/409 |

FOREIGN PATENT DOCUMENTS

| | | |
|---|---|---|
| EP | 0 147 052 A2 | 7/1985 |
| EP | 2090164 B1 | 12/2011 |
| WO | 2015/189320 A1 | 12/2015 |
| WO | 2015/189321 A1 | 12/2015 |

OTHER PUBLICATIONS

J. Lechevin et al.: "Activity of LM 2219 (Difethialone), a new anticoagulant Rodenticide, IN Commensal Rodents", Vertebrate pest conference proceedings, vol. 2219, 1988, pp. 59-63, XP055272711.
International Search Report, dated Feb. 15, 2017, from corresponding PCT/EP2016/079859 application.

* cited by examiner

Primary Examiner — Johann R Richter
Assistant Examiner — Genevieve S Alley
(74) Attorney, Agent, or Firm — IPSilon USA, LLP (57) ABSTRACT

Disclosed is to a composition including difethialone, containing a configurational stereoisomer of difethialone, referred to as a hetero-stereoisomer, of formula 3-(4'-bromobiphenyl-4-yl)-1-(4-hydroxythiocoumarin-3-yl)-1,2,3,4-tetrahydronaphthalene, in which the carbon atoms 1 and 3 of the 1,2,3,4-tetrahydronaphthalene group have different absolute configurations, the composition including an amount of a dextrorotatory enantiomer of the hetero-stereoisomer such that the ratio of this amount to the amount of difethialone in the composition is less than 10%; the amount of the dextrorotatory enantiomer of the hetero-stereoisomer of difethialone in the composition being different from the amount of levorotatory enantiomer of the hetero-stereoisomer of difethialone in the composition.

20 Claims, 4 Drawing Sheets a1)

COMPOSITION AND RODENTICIDE BAIT COMPRISING DIFETHIALONE AND METHOD FOR CONTROLLING TARGET RODENT PESTS

The invention relates to a composition comprising difethialone, to a rodenticidal bait comprising such a composition and to a process for controlling target rodent pests. The invention thus relates to the technical field of controlling populations of target rodent pests.

It is known practice to use rodenticidal baits as poisons for target rodent pests. It is known from EP 2 090 164 that difethialone is a second-generation anticoagulant acting in a single dose. US 2005/181003 describes a rodenticidal bait in gel form comprising difethialone in a mass proportion of 25 ppm.

Such a bait is liable to be consumed by animals other than target rodent pests when it is made available to target rodent pests. It may be consumed directly (primary consumption) by domestic animals or pets. It may also be consumed accidentally by humans. Such consumption may result in poisoning, which may be lethal, of these domestic animals, pets or humans.

In addition, a fraction of the difethialone of these rodenticidal baits may be ingested (secondary consumption) by animals—especially by birds—which prey on weakened rodent pests that have consumed such a rodenticidal bait, or by animals which carrion-feed on rodent pests that have died from having consumed such a rodenticidal bait. This secondary consumption is liable in the long term to result in the death of these predatory or carrion-feeding animals, which may be animals—especially birds—belonging to protected species.

The invention is thus directed towards overcoming these drawbacks by proposing a composition comprising difethialone, a rodenticidal bait comprising such a composition and a process for controlling target rodent pests, which are not only effective for controlling the populations of target rodent pests but can also limit the risks of poisoning of non-target animals—especially domestic animals, pets or humans— accidentally consuming such a rodenticidal bait and the risks of poisoning by secondary consumption of domestic animals (pets or reared animals) or wild animals—for example foxes or birds—which prey on target rodent pests that have consumed the rodenticidal bait or which carrion—feed on target rodent pests that have died by poisoning.

The invention is also directed towards proposing a composition comprising difethialone, a rodenticidal bait comprising such a composition and a process for controlling target rodent pests, the use of which is in accordance with the rules of good practice, especially with respect to the protection of birds, and in particular birds of prey.

The invention is also directed towards a composition comprising difethialone, a rodenticidal bait comprising such a composition and a process for controlling target rodent pests, which only require low doses of difethialone to control a population of target rodent pests, and which are friendly towards the environment and the health of humans and non-target animals—especially birds.

The invention is also directed towards proposing a composition comprising difethialone, a rodenticidal bait comprising such a composition and a process for controlling target rodent pests, which are able to be used for controlling target rodent pests that are resistant to known baits for controlling target rodent pests.

The invention is also directed towards proposing an alternative to known rodenticidal agents and rodenticidal baits.

To do this, the invention relates to a composition comprising difethialone, characterized in that it comprises a configurational stereoisomer of difethialone, named hetero-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have different absolute configurations (1R,3S or 1S,3R), said composition comprising an amount of dextrorotatory enantiomer of said hetero-stereoisomer such that the ratio of this amount to the amount of difethialone in the composition is less than 10%; the amount of the dextrorotatory enantiomer of said hetero-stereoisomer of difethialone in the composition being different from the amount of laevorotatory enantiomer of said hetero-stereoisomer of difethialone in the composition.

Throughout the text:
the term "difethialone" denotes the compound 3-(4'-bromobiphenyl-4-yl)-1-(4-hydroxythiocoumarin-3-yl)-1,2,3,4-tetrahydronaphthalene or 3-[3[4-(4-bromophenyl)phenyl]-1-tetralinyl]-2-hydroxy-4-thiochromenone or 3-[3-(4'-bromo[1,1'-biphenyl]-4-yl)-1,2,3,4-tetrahydro-1-naphthalenyl]-4-hydroxy-2H-1-benzothiopyran-2-one of formula (I) below:

in which the numbers of carbons 1 and 3 of the 1,2,3,4-tetrahydronaphthalene group are indicated;

the term "stereoisomers" denotes isomers of the same semi-structural formula, but in which the relative position of the atoms differs in space. The term "configurational stereoisomers" denotes stereoisomers for which conversion from one to the other of these configurational stereoisomers requires the cleavage/reformation of an interatomic covalent bond. Thus, the term "configurational stereoisomers" denotes stereoisomers which are not conformational isomers (or "rotamers", for which conversion from one to the other of the conformational isomers is accompanied only by rotation of a part of the molecule about the axis of a σ (sigma) bond formed by axial orbital overlap);

the term "hetero-stereoisomer" of difethialone denotes the configurational stereoisomer of difethialone of formula 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group of said hetero-stereoisomer have different absolute configurations (1R,3S and 1S,3R), said absolute configurations being determined according to the sequential priority rules and the Cahn-Ingold-Prelog (CIP) nomenclature;

the term "homo-stereoisomer" of difethialone denotes the configurational stereoisomer of difethialone of formula 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group of said homo-stereoisomer have the same absolute configuration (1R,3R and 1S,3S); and the term "amount" means a molar amount, a mass amount or a volume amount. The proportions are thus proportions of a molar amount relative to a molar amount, of a mass amount relative to a mass amount, or of a volume amount relative to a volume amount;

the term "substantially" indicates, in the usual manner, that a structural or functional characteristic should not be taken as marking an abrupt discontinuity, which would have no physical meaning, but covers not only this structure or this function, but also slight variations of this structure or of this function which produce, in the technical context under consideration, an effect of the same nature, or else of the same degree;

the expressions "high-pressure liquid chromatography" or "high-performance liquid chromatography" (HPLC) denote "HPLC" chromatography or "High-Performance Liquid Chromatography"; and the term "retention time" denotes the time, measured at the top of the peak in the chromatogram, for which a compound is retained on a chromatography column.

In a composition according to the invention:
said hetero-stereoisomer of difethialone is present in the form of an amount $Q_D$ of a dextrorotatory enantiomer and of an amount $Q_L$ of a laevorotatory enantiomer; and
said homo-stereoisomer of difethialone is present in the form of an amount $Q'_D$ of a dextrorotatory enantiomer and of an amount $Q'_L$ of a laevorotatory enantiomer.

In this composition, the proportion:

$$\frac{QD}{QD + QL + Q'D + Q'L}$$

is greater than or equal to 0 and strictly less than 10%, with $Q_L \neq Q_D$.

A composition according to the invention comprises an amount of the dextrorotatory enantiomer of said hetero-stereoisomer of difethialone such that the ratio of this amount to the amount of difethialone is less than 10%, with the exclusion of a composition comprising:
an amount of said homo-stereoisomer of difethialone such that the ratio of this amount to the amount of (total) difethialone in the composition is between 80%—limit included—and 100%—limit included—; and
an amount of a racemic mixture of the enantiomers of said hetero-stereoisomer of difethialone such that the ratio of this amount to the amount of (total) difethialone in the composition is between 0%—limit included—and 20%—limit excluded.

A composition according to the invention may be free of dextrorotatory enantiomer of said hetero-stereoisomer of difethialone. The composition may also comprise the dextrorotatory enantiomer of said hetero-stereoisomer of difethialone in trace amount. Such a composition substantially free of dextrorotatory enantiomer of said hetero-stereoisomer of difethialone comprises a non-zero proportion of laevorotatory enantiomer of said hetero-stereoisomer of difethialone.

The inventors have succeeded in separating the laevorotatory and dextrorotatory enantiomers of said hetero-stereoisomer of difethialone and the laevorotatory and dextrorotatory enantiomers of said homo-stereoisomer of difethialone by high-pressure liquid chromatography in isocratic mode and under particular conditions by using a chromatography column comprising a chiral stationary phase. Specifically, it was not known at the date of the invention how to separate the laevorotatory and dextrorotatory enantiomers of said homo-stereoisomer of difethialone and the laevorotatory and dextrorotatory enantiomers of said hetero-stereoisomer of difethialone.

They were able to perform this separation using a LUX® Cellulose-3 HPLC column (Phenomenex, Le Pecq, France) of dimensions 150×2 mm and comprising a chiral stationary phase constituted of porous particles of cellulose tris(4-methylbenzoate), with a particle size of 3 µm and a porosity of 1000 Å and using, as mobile phase, an eluent obtained by mixing acetonitrile (A) and water comprising formic acid in a volume proportion of 0.1% in the water (B), the AB volume ratio being 80/20. The flow rate of the mobile phase in the column is maintained at a value of 0.25 mL/minute and the separation is performed at a temperature of 23.2° C. The composition to be analysed is at a concentration of 1 µg of difethialone per millilitre of acetonitrile and the volume injected onto the column is 1 µL. The detection is performed by tandem mass spectrometry (MS/MS) or by spectrophotometry, adjusting the concentration of difethialone and the injection volume for the purpose of optimum detection.

Under these conditions, the value of the retention time ($t_3$) for the dextrorotatory enantiomer of said hetero-stereoisomer of difethialone may vary according to the operating conditions—especially according to the column temperature conditions—and may be between 11.3 minutes and 11.8 minutes. The value of the retention time ($t_2$) for the laevorotatory enantiomer of said hetero-stereoisomer of difethialone may vary according to the operating conditions—especially according to the column temperature conditions—and may be between 9.0 minutes and 9.5 minutes, such that the dextrorotatory and laevorotatory enantiomers of said hetero-stereoisomer may be separated by high-pressure liquid chromatography on a chiral column.

The value of the retention time ($t_1$) for the laevorotatory enantiomer of said homo-stereoisomer may vary according to the operating conditions—especially according to the column temperature conditions—and may be between 7.8 minutes and 8.2 minutes. The value of the retention time ($t_4$) for the dextrorotatory enantiomer of said homo-stereoisomer according to the invention may vary according to the operating conditions—especially according to the column temperature conditions—and may be between 14.0 minutes and 14.4 minutes, such that the dextrorotatory and laevorotatory enantiomers of said homo-stereoisomer may be separated by high-pressure liquid chromatography on a chiral column.

Thus, under these analytical conditions, the order of elution of the configurational stereoisomers of difethialone is such that $t_1 < t_2 < t_3 < t_4$. The retention time values $t_1$, $t_2$, $t_3$ and $t_4$ are liable to vary, especially according to the chromatography conditions and according to the temperature of the chromatography column. However, under these chromatography conditions, the order of elution of the configurational stereoisomers of difethialone remains unchanged.

The amount of each configurational stereoisomer of difethialone is measured from a chromatogram by evaluating the area under the peak corresponding to each enantiomer and, where appropriate, by comparing this area measurement with the areas obtained by analysis of samples comprising known amounts of configurational stereoisomers of difethialone.

Optical Rotation of the Configurational Stereoisomers

The optical rotation of each of the configurational stereoisomers of difethialone dissolved in chloroform ($CHCl_3$) is measured by means of a P 2000 digital polarimeter (JASCO, Bouguenais, France) operating with excitatory light with a wavelength of 589 nm.

The mean optical rotation α (calculated on two series of ten measurements) of a solution of dextrorotatory enantiomer of said homo-stereoisomer of difethialone at 11.6 g/L in chloroform is 2.308°. The specific optical rotation at 25° C. $[\alpha]^{25°\ C.}_{589\ nm}$ for the dextrorotatory enantiomer of said homo-stereoisomer of difethialone, measured on the sodium D line (589 nm), is +19.9°.

The mean optical rotation α (calculated on two series of ten measurements) of a solution of laevorotatory enantiomer of said homo-stereoisomer of difethialone at 11.05 g/L in chloroform is −1.635°. The specific optical rotation at 25° C. $[\alpha]^{25°\ C.}_{589\ nm}$ for the laevorotatory enantiomer of said homo-stereoisomer of difethialone, measured on the sodium D line (589 nm), is −14.8°.

The mean optical rotation α (calculated on two series of ten measurements) of a solution of dextrorotatory enantiomer of said hetero-stereoisomer of difethialone at 6.3 g/L in chloroform is +0.573°. The specific optical rotation at 25° C. $[\alpha]^{25°\ C.}_{589\ nm}$ for the dextrorotatory enantiomer of said hetero-stereoisomer of difethialone, measured on the sodium D line (589 nm), is +9.1°.

The mean optical rotation α (calculated on two series of ten measurements) of a solution of laevorotatory enantiomer of said hetero-stereoisomer of difethialone at 6.3 g/L in chloroform is −0.904° The specific optical rotation at 25° C. $[\alpha]^{25°\ C.}_{589\ nm}$ for the laevorotatory enantiomer of said hetero-stereoisomer of difethialone, measured on the sodium D line (589 nm), is −13°.

Circular Dichroism of the Configurational Stereoisomers

The dextrorotatory enantiomer of said homo-stereoisomer of difethialone, dissolved in methanol at a concentration of 0.96 g/L and placed in a quartz spectrophotometry cuvette, has a circular dichroism spectrum acquired at 25° C. with positive circular dichroism values between 220 nm and 300 nm.

The laevorotatory enantiomer of said homo-stereoisomer of difethialone, dissolved in methanol at a concentration of 0.81 g/L and placed in a quartz spectrophotometry cuvette, has a circular dichroism spectrum acquired at 25° C. with negative circular dichroism values between 220 nm and 300 nm.

The dextrorotatory enantiomer of said hetero-stereoisomer of difethialone, dissolved in methanol ($CH_3OH$) at a concentration of 0.65 g/L and placed in a quartz spectrophotometry cuvette, has a circular dichroism spectrum acquired at 25° C. with positive circular dichroism values between 210 nm and 250 nm and between 270 nm and 300 nm.

The laevorotatory enantiomer of said hetero-stereoisomer of difethialone, dissolved in methanol at a concentration of 0.94 g/L and placed in a quartz spectrophotometry cuvette, has a circular dichroism spectrum acquired at 25° C. with negative circular dichroism values between 225 nm and 250 nm.

Proton Nuclear Magnetic Resonance

Said homo-stereoisomer of difethialone has, on proton nuclear magnetic resonance ($^1$H-NMR) spectroscopy at 300 MHz in $CDCl_3$, a multiplet with a chemical shift (δ) of between 4.9 ppm and 5.1 ppm corresponding to carbon 1 of the 1,2,3,4-tetrahydronaphthalene group of said homo-stereoisomer of difethialone. The laevorotatory and dextrorotatory enantiomers of said homo-stereoisomer of difethialone are not distinguishable by proton NMR.

Said hetero-stereoisomer of difethialone has, on proton nuclear magnetic resonance ($^1$H-NMR) spectroscopy at 300 MHz in $CDCl_3$, a multiplet with a chemical shift (δ) of about 5.3 ppm corresponding to carbon 1 of the 1,2,3,4-tetrahydronaphthalene group of said homo-stereoisomer of difethialone. The laevorotatory and dextrorotatory enantiomers of said hetero-stereoisomer of difethialone are not distinguishable by proton NMR.

The inventors who succeeded in separating the configurational stereoisomers of difethialone observed, entirely surprisingly, that the configurational stereoisomers of difethialone do not have the same hepatic persistence in target rodent pests and that the dextrorotatory enantiomer of said hetero-stereoisomer of difethialone has higher hepatic persistence in target rodent pests than that of the laevorotatory enantiomer of said hetero-stereoisomer of difethialone and higher than that of the dextrorotatory and laevorotatory enantiomers of said homo-stereoisomer of difethialone.

The dextrorotatory enantiomer of said hetero-stereoisomer of difethialone persists in the liver of target rodent pests for longer than the other enantiomers, such that a dead or live target rodent pest which has ingested the dextrorotatory enantiomer of said hetero-stereoisomer of difethialone constitutes a toxic prey (a poison) for non-rodent mammals and birds which consume said target rodent pest—dead or alive—and in particular for predators (especially non-rodent mammals and birds) which preferentially consume the viscera of their prey and in particular the liver of their prey.

The inventors have also observed that a composition and a rodenticidal bait according to the invention containing a reduced amount of dextrorotatory enantiomer of said hetero-stereoisomer of difethialone such that the ratio of this amount to the amount of difethialone is less than 10%—said dextrorotatory enantiomer of said hetero-stereoisomer of difethialone being the enantiomer with the highest hepatic persistence—in fact makes it possible, entirely surprisingly, to efficiently control target rodent pests.

The invention thus relates to a composition and a rodenticidal bait comprising difethialone in which the amount of the configurational stereoisomer of difethialone with the highest hepatic persistence in target rodent pests is such that the ratio of this amount to the amount of difethialone is less than 10%.

Advantageously and according to the invention, the composition comprises an amount of dextrorotatory enantiomer of said hetero-stereoisomer such that the ratio of this amount of dextrorotatory enantiomer of said hetero-stereoisomer to the (total) amount of difethialone is less than 9%, especially less than 7%, preferably less than 5%, more preferentially less than 4%, even more preferentially less than 3%. Advantageously and according to the invention, the composition may comprise an amount of dextrorotatory enantiomer of said hetero-stereoisomer such that the ratio of this amount of dextrorotatory enantiomer of said hetero-stereoisomer to the total amount of difethialone is less than 2%, in particular less than 1%.

Advantageously and as a variant according to the invention, the composition may comprise an amount of laevorotatory enantiomer of a configurational stereoisomer of difethialone, named homo-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have the same absolute configuration (1S,3S or 1R,3R), the amount of said laevorotatory enantiomer of said homo-stereoisomer in the composition being such that the ratio of this amount to the total amount of difethialone in the composition is less than 10%.

The inventors who succeeded in separating the configurational stereoisomers of difethialone also determined that the laevorotatory enantiomer of said homo-stereoisomer of difethialone is in fact the enantiomer of the homo-stereoisomer of difethialone which has the highest hepatic persistence in target rodent pests. They also observed that the laevorotatory enantiomer of said homo-stereoisomer of difethialone is the most persistent in the liver of target rodent pests from among the enantiomers of said homo-stereoisomer of difethialone and the laevorotatory enantiomer of said hetero-stereoisomer of difethialone.

Advantageously and according to this variant of the invention, the composition may comprise an amount of laevorotatory enantiomer of said homo-stereoisomer such that the ratio of this amount of laevorotatory enantiomer of said homo-stereoisomer to the total amount of difethialone is less than 9%, especially less than 7%, preferably less than 5%, more preferentially less than 4%, even more preferentially less than 3%. Advantageously and according to the invention, the composition comprises an amount of laevorotatory enantiomer of said homo-stereoisomer such that the ratio of this amount of laevorotatory enantiomer of said homo-stereoisomer to the total amount of difethialone is less than 2%, in particular less than 1%. The composition may also be free of laevorotatory enantiomer of said homo-stereoisomer of difethialone. The composition may also comprise the laevorotatory enantiomer of said homo-stereoisomer of difethialone in trace amount in the composition.

Advantageously and in another variant according to the invention, the composition may comprise an amount of laevorotatory enantiomer of a configurational stereoisomer of difethialone, named homo-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have the same absolute configuration (1S,3S or 1R,3R), the amount of said homo-stereoisomer being such that the ratio of this amount to the total amount of difethialone in the composition is between 10% (limit included) and 100% (limit included), especially between 30% and 100%, in particular between 90% and 100%.

Advantageously and as a variant according to the invention, the composition may also comprise an amount of the laevorotatory enantiomer of said hetero-stereoisomer of difethialone in the composition such that the ratio of this amount to the total amount of difethialone in the composition is less than 10%.

The inventors who succeeded in separating the configurational stereoisomers of difethialone, and who observed that the configurational stereoisomers of difethialone do not have the same hepatic persistence in target rodent pests, also determined that the laevorotatory enantiomer of said hetero-stereoisomer of difethialone is in fact the enantiomer that is the most persistent in the liver of target rodent pests from among the laevorotatory enantiomer of said hetero-stereoisomer of difethialone and the dextrorotatory enantiomer of said hetero-stereoisomer of difethialone.

Advantageously and according to this variant of the invention, the composition may comprise an amount of laevorotatory enantiomer of said hetero-stereoisomer such that the ratio of this amount of laevorotatory enantiomer of said hetero-stereoisomer to the total amount of difethialone is less than 9%, especially less than 7%, preferably less than 5%, more preferentially less than 4%, even more preferentially less than 3%. Advantageously and according to the invention, the composition comprises an amount of laevorotatory enantiomer of said hetero-stereoisomer such that the ratio of this amount of laevorotatory enantiomer of said hetero-stereoisomer to the total amount of difethialone is less than 2%, in particular less than 1%. The composition may also be free of laevorotatory enantiomer of said hetero-stereoisomer of difethialone, i.e. the laevorotatory enantiomer of said hetero-stereoisomer of difethialone may be present in the composition, but only in trace amount.

Advantageously and according to another variant of the invention, the composition may comprise an amount of the laevorotatory enantiomer of said hetero-stereoisomer of difethialone such that the ratio of this amount to the total amount of difethialone is between 10% (limit included) and 100% (limit included), especially between 30% and 100%, in particular between 90% and 100%.

Advantageously and as a variant according to the invention, the composition may comprise an amount of the dextrorotatory enantiomer of said homo-stereoisomer of difethialone such that the ratio of this amount to the total amount of difethialone in the composition is less than 10%.

However, advantageously and as a variant according to the invention, there is nothing to prevent the composition from comprising an amount of dextrorotatory enantiomer of said homo-stereoisomer of difethialone such that the ratio of this amount to the total amount of difethialone in the composition is between 10% (limit included) and 100% (limit included), especially between 30% and 100%, in particular between 90% and 100%.

Advantageously and according to the invention, the composition is in liquid form and comprises a liquid solvent for difethialone. It may also be a suspension or an emulsion of difethialone in a liquid medium.

The invention also relates to the use of a composition according to the invention for the preparation of a rodenticidal bait for target rodent pests.

The invention also relates to a rodenticidal bait comprising a composition according to the invention, and at least one excipient that is edible for target rodent pests.

The invention thus relates to a rodenticidal bait comprising difethialone and at least one excipient that is edible for target rodent pests, characterized in that it comprises a configurational stereoisomer of difethialone, named hetero-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have different absolute configurations (1R,3S or 1S,3R), the rodenticidal bait comprising an amount of dextrorotatory enantiomer of said hetero-stereoisomer such that the ratio of this amount to the amount of difethialone in the rodenticidal bait is less than 10%; the amount of dextrorotatory enantiomer of said hetero-stereoisomer of difethialone in the rodenticidal bait being different from the amount of laevorotatory enantiomer of said hetero-stereoisomer of difethialone in the rodenticidal bait.

Advantageously, a rodenticidal bait according to the invention comprises an amount of dextrorotatory enantiomer of said hetero-stereoisomer such that the ratio of this amount to the total amount of difethialone in the rodenticidal bait is less than 10% and with the exclusion of a racemic mixture of the dextrorotatory and laevorotatory enantiomers of said hetero-stereoisomer of difethialone.

Advantageously and as a variant according to the invention, the rodenticidal bait comprises a configurational stereoisomer of difethialone, named homo-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have the same absolute configuration (1S,3S or 1R,3R), the rodenticidal bait comprising an amount of a laevorotatory enantiomer of said homo-stereoisomer of difethialone such that the ratio of the amount of laevorotatory enantiomer of said homo-stereoisomer of difethialone to the total amount of difethialone in the rodenticidal bait is less than 10%.

Advantageously and as a variant according to the invention, a rodenticidal bait comprising difethialone according to the invention comprises:
  an excipient that is edible for target rodent pests; and
  an amount of the dextrorotatory enantiomer of said hetero-stereoisomer such that the ratio of this amount to the total amount of difethialone in the rodenticidal bait is less than 10%; and
  an amount of the laevorotatory enantiomer of said homo-stereoisomer such that the ratio of the amount of laevorotatory enantiomer of said homo-stereoisomer to the total amount of difethialone is less than 10%.

Advantageously and according to the invention, the rodenticidal bait comprises an amount of a laevorotatory enantiomer of said hetero-stereoisomer of difethialone such that the ratio of the amount of the laevorotatory enantiomer of said hetero-stereoisomer of difethialone in the rodenticidal bait to the total amount of difethialone in the rodenticidal bait is less than 10%.

Advantageously and as a variant, a rodenticidal bait according to the invention comprises:
  an excipient that is edible for target rodent pests; and
  an amount of the dextrorotatory enantiomer of said hetero-stereoisomer such that the ratio of this amount to the amount of difethialone in the rodenticidal bait is less than 10%; and
  an amount of the laevorotatory enantiomer of said homo-stereoisomer such that the ratio of the amount of laevorotatory enantiomer of said homo-stereoisomer to the amount of difethialone in the rodenticidal bait is less than 10%; and
  an amount of the laevorotatory enantiomer of said hetero-stereoisomer of difethialone such that the ratio of this amount of laevorotatory enantiomer of said hetero-stereoisomer of difethialone to the amount of difethialone in the rodenticidal bait is less than 10%.

Advantageously and according to the invention, the rodenticidal bait comprises a mass amount of difethialone such that the ratio (mass proportion) of this mass amount of difethialone to the mass amount of the rodenticidal bait is less than 200 ppm, i.e. less than 200 mg of difethialone per kilogram of rodenticidal bait. Advantageously, the mass proportion of difethialone is between 1 ppm and 200 ppm (1 mg to 200 mg of difethialone per kilogram of rodenticidal bait), especially between 1 ppm and 100 ppm (1 mg to 100 mg of difethialone per kilogram of rodenticidal bait), preferably between 5 ppm and 50 ppm (5 mg to 50 mg of difethialone per kilogram of rodenticidal bait), more preferentially between 5 ppm and 25 ppm (5 mg to 25 mg of difethialone per kilogram of rodenticidal bait), even more preferentially about 15 ppm (15 mg of difethialone per kilogram of rodenticidal bait).

Advantageously and according to the invention, the excipient that is edible for target rodent pests is chosen to allow consumption of the bait by target rodent pests. Advantageously and according to the invention, each edible excipient is non-lethal to target rodent pests. The edible excipient is not in itself rodenticidal.

Advantageously and according to the invention, the edible excipient comprises at least one food chosen from the group formed from cereal seeds, especially hulled cereal seeds, cereal seed meals, cereal seed flours, cereal seed flakes, cereal bran and non-cereal seeds, for example alfalfa seeds, especially in hulled form, in the form of meal, in the form of flour, or in the form of flakes or bran. The edible excipient may comprise any support that can be consumed by target rodent pests.

Advantageously, the edible excipient comprises at least one food chosen from the group formed from foods of plant origin and foods of animal origin. Advantageously, the edible excipient comprises at least one food chosen to stimulate the appetite of target rodent pests. In particular, this food is chosen from the group formed from seeds of one or more cereals, hulled seeds of one or more cereals, meals of seeds of one or more cereals, flakes of seeds of one or more cereals, bran of one or more cereals and flour of seeds of one or more cereals. By way of example, the cereals are chosen from the group formed from oat, wheat, barley, corn, soybean and rice.

Advantageously, the food is chosen from the group formed from sweetened foods. For example, they may be foods comprising at least one sugar chosen from the group formed from sucrose, lactose, fructose and glucose. It may be a sugar syrup—for example a sugar syrup obtained by hydrolysis of starch—or a sugar syrup obtained by hydrolysis of sucrose (invert sugar syrup), or a beet sugar syrup, or a maple syrup or a sugarcane syrup, or a syrup obtained from a plant of the Stevia genus.

Advantageously, the food is chosen from the group formed from coconut albumen (copra) flakes and flour. Advantageously, the food is chosen from the group formed from walnuts, hazelnuts and almonds—in grated and/or powder form.

Advantageously, the food is chosen from the group formed from plant fats, plant oils (for example rapeseed oil, soybean fat, sunflower oil, cocoa butter, groundnut oil, groundnut butter, corn oil, palm oil), animal fats and animal oils (butter, lard, fish oil).

Advantageously, the food is chosen from the group formed from proteins of plant origin and proteins of animal origin. By way of example, examples that may be mentioned include powdered milk, especially powdered skimmed milk, eggs, especially powdered eggs, protein hydrolysates of animal origin and protein hydrolysates of plant origin.

Advantageously and according to the invention, the rodenticidal bait is chosen from the group formed from solid baits comprising difethialone and a solid edible excipient. Advantageously, the rodenticidal bait is a solid in divided form, for example in the form of balls or granules. Advantageously, the rodenticidal bait may be a solid in block or paste form that may be consumed by target rodent pests or a solid material that may be nibbled by target rodent pests. Advantageously, the solid rodenticidal bait according to the invention may be in the form of a rigid block, a semi-rigid block, a foam, a powder or a gel.

Advantageously, the rodenticidal bait which is in the form of a powder, in the form of a foam or in the form of a gel is suitable for soiling the fur of the target rodent pest(s) and for being ingested by said pest(s) during their grooming.

Advantageously and according to the invention, the rodenticidal bait is chosen from the group formed from liquid baits comprising difethialone and a liquid edible excipient. The rodenticidal bait is then a drink for target rodent pests. It may be a suspension of difethialone in solid form in a liquid edible excipient or an emulsion of difethialone in a liquid medium.

Advantageously, the rodenticidal bait comprises at least one dye. Such a dye makes it possible in particular to give said rodenticidal bait a colour that is readily detectable and identifiable by a person handling the rodenticidal bait.

Advantageously, the rodenticidal bait comprises at least one preserving agent capable of ensuring its conservation during its storage. Advantageously, the rodenticidal bait comprises at least one bittering compound such as denatonium benzoate, also known as Bitrex®, which is intended to reduce the risks of accidental consumption by non-target organisms.

Advantageously, in one particular variant, the composition and the rodenticidal bait according to the invention exclusively comprise difethialone as rodenticidal substance. In particular, the composition and the rodenticidal bait according to the invention are free of any other anticoagulant substance for rodenticidal use. However, in this variant according to the invention, the composition and the rodenticidal bait may comprise any pest-control substance other than a rodenticide, such as an insecticidal and/or acaricidal substance.

Advantageously, in another particular variant, the composition and the rodenticidal bait according to the invention comprise difethialone and at least one other substance different from difethialone as rodenticidal substance. This other rodenticidal substance different from difethialone may be another anticoagulant substance—especially of the anti-vitamin K type or not—or another non-anticoagulant rodenticidal substance.

The invention also relates to a process for controlling target rodent pests, in which there is spread an amount of rodenticidal bait according to the invention.

The invention thus relates to a process for controlling target rodent pests, in which there is spread an amount of rodenticidal bait comprising difethialone and:
  at least one excipient that is edible for target rodent pests; and
  a configurational stereoisomer of difethialone, named hetero-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have different absolute configurations (1R,3S or 1S,3R), the rodenticidal bait comprising an amount of a dextrorotatory enantiomer of said hetero-stereoisomer such that the ratio of this amount to the amount of difethialone in the rodenticidal bait is less than 10%; the amount of the dextrorotatory enantiomer of said hetero-stereoisomer of difethialone in the rodenticidal bait being different from the amount of laevorotatory enantiomer of said hetero-stereoisomer of difethialone in the rodenticidal bait.

The invention also relates to a process for controlling target rodent pests, in which there is spread an amount of rodenticidal bait according to the invention comprising an amount of the dextrorotatory enantiomer of said hetero-stereoisomer of difethialone in a proportion of less than 10% relative to the amount of difethialone, the amount of bait being sufficient to be rodenticidal.

An amount of rodenticidal bait comprising difethialone, which has reduced persistence in the liver of target rodent pests relative to the hepatic persistence of difethialone but sufficient rodenticidal efficacy to control target rodent pests, is thus spread. The process according to the invention thus makes it possible to limit the secondary poisoning of non-rodent mammals and birds that are liable to preferentially consume the viscera—in particular the liver—of said poisoned rodents which are dead or alive but comprising a reduced amount—and especially a non-lethal amount—of difethialone.

Advantageously and as a variant according to the invention, the following are chosen in combination:
  the edible excipient;
  a proportion of each of the configurational stereoisomers of difethialone relative to the difethialone; and
  a mass proportion of difethialone relative to the rodenticidal bait; and
  an amount of spread bait;
so that target rodent pests consume an amount of difethialone that is sufficient to be lethal to said target rodent pests which consume said bait in the course of a single period of 24 consecutive hours.

A rodenticidal bait according to this variant of the invention is a bait that is mortal in a single intake, or a "one-shot" bait. Advantageously and according to this variant of the invention, the mass proportion of difethialone in the rodenticidal bait is between 5 ppm and 200 ppm, especially between 5 ppm and 100 ppm, preferably between 5 ppm and 50 ppm, more preferentially between 15 ppm and 50 ppm.

Advantageously and in another variant according to the invention, the following are chosen in combination:
  the edible excipient;
  a proportion of each of the configurational stereoisomers of difethialone relative to the difethialone; and
  a mass proportion of difethialone relative to the rodenticidal bait; so that target rodent pests consume an amount of difethialone:
    which is non-lethal to target rodent pests, i.e. which is generally non-lethal to target rodent pests which consume said bait over a single period of 24 consecutive hours; and
    which is sufficient to be lethal to target rodent pests which consume said bait over several 24-hour periods, said periods being consecutive.

This other variant of the invention is thus also directed towards a process for controlling target rodent pests, in which there is spread an amount of rodenticidal bait that is lethal to target rodent pests durably consuming this rodenticidal bait and generally non-lethal to non-target rodents or animals accidentally consuming this rodenticidal bait. This is then referred to as a "multi-dose" or "multi-feeding" control process. In such a process according to the invention, the consumption of rodenticidal bait by a target rodent pest over a period of 24 hours is insufficient to result in the death of said rodent, whereas repeated consumption of rodenticidal bait over at least two consecutive days results in the death of the target rodent pest.

This other variant of the invention is thus directed towards a process for controlling a population of target rodent pests, in which target rodent pests are provided with an amount of rodenticidal bait that is liable to be ingested by the target rodent pests, the amount of rodenticidal bait being sufficient to kill target rodent pests which consume said rodenticidal bait over several days.

Advantageously, the amount of rodenticidal bait spread, the mass proportion of difethialone in the rodenticidal bait and the proportion of each configurational stereoisomer of difethialone in the difethialone are adapted so that the consumption of the rodenticidal bait is lethal to target rodent pests which daily consume bait over at least two 24-hour periods, especially from 3 to 7 periods, said periods being consecutive.

Advantageously and in this other variant according to the invention, the mass proportion of difethialone is between 5 ppm and 50 ppm, especially between 5 ppm and 30 ppm—especially about 15 ppm—relative to the rodenticidal bait.

In a process according to the invention, target rodent pests are provided with an amount of rodenticidal bait comprising difethialone of low hepatic persistence in target rodent pests, the amount of rodenticidal bait being sufficient to satisfy the daily appetite of the target rodent pests, said rodenticidal bait comprising an amount of the dextrorotatory enantiomer of said hetero-stereoisomer of difethialone such that the ratio of this amount to the amount of difethialone is less than 10%.

In a process according to the invention, the amount of rodenticidal bait spread, the proportion of each configurational stereoisomer of difethialone relative to the difethialone and the mass proportion of difethialone relative to the rodenticidal bait are adapted so as to allow consumption of rodenticidal bait for several days by target rodent pests, while at the same time limiting:
- the risks of primary intoxication of non-target mammals and birds which are liable to consume such a rodenticidal bait only occasionally and accidentally;
- the risks of secondary intoxication, for example of predators of target rodents, which are liable to consume target rodents—dead or live—that have ingested an amount of said bait.

The invention also relates to a chromatographic process for separating the configurational stereoisomers of difethialone, in which:
- a high-pressure liquid chromatography column of dimensions 150×2 mm and comprising a chiral stationary phase constituted of cellulose tris(4-methylbenzoate) particles, said particles having a mean size of 3 μm and having a mean pore size of 1000 Å, is chosen;
- a mixture formed from acetonitrile (A) and water comprising 0.1% by volume of formic acid (B), with an A/B volume ratio of 80/20 and with a flow rate of the liquid mobile phase in the chromatography column of 0.25 mL/minute, is chosen as liquid mobile phase;
- separation of the configurational stereoisomers of difethialone is performed at room temperature, during which:
  - a liquid composition comprising difethialone is introduced into the top of the chromatography column; and then
  - the liquid composition is entrained with the mobile phase in the chromatography column under conditions suitable for separating the configurational stereoisomers of difethialone; and then
  - at least one fraction of the mobile phase is collected, comprising a configurational stereoisomer of difethialone separated from the other configurational stereoisomers of difethialone different from the collected configurational stereoisomer; and
  - the liquid mobile phase of said collected fraction is removed so as to obtain the collected configurational stereoisomer of difethialone.

The invention also relates to an isolated configurational stereoisomer of difethialone obtained via a process according to the invention.

The invention also relates to a configurational stereoisomer of difethialone, to a process for obtaining such a configurational stereoisomer of difethialone, to a composition and a rodenticidal bait comprising such a configurational stereoisomer and to a process for controlling target rodent pests, characterized in combination by all or some of the characteristics mentioned hereinabove or hereinbelow.

Other aims, characteristics and advantages of the invention will emerge on reading the following description and the examples, which are given for purely non-limiting purposes and which refer to the attached figures, in which.

A. PURIFICATION OF THE CONFIGURATIONAL STEREOISOMERS OF DIFETHIALONE

Figure 1:
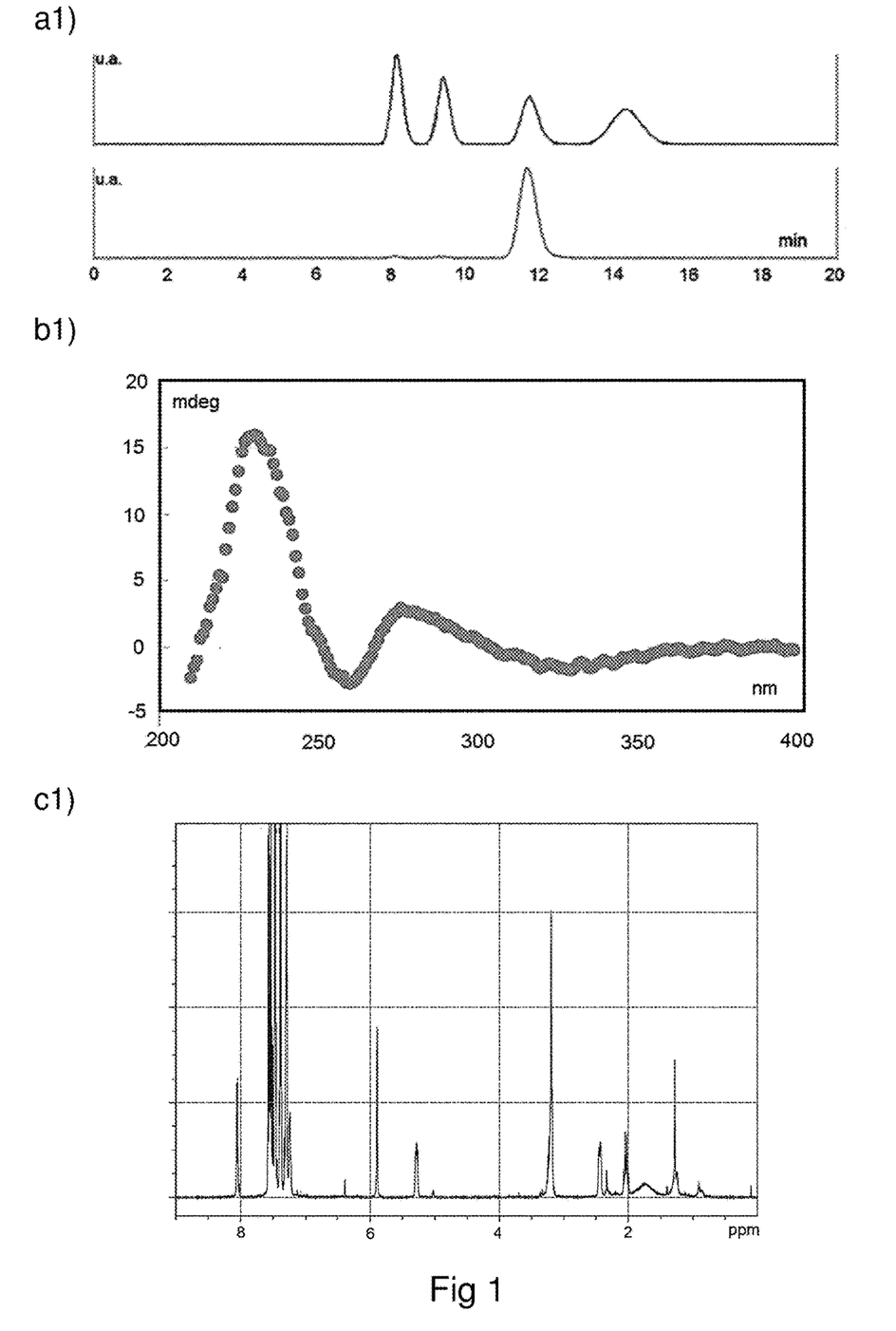
FIG. 1 relates to the dextrorotatory enantiomer of said hetero-stereoisomer of difethialone—FIG. a1) represents an analysis by high-pressure liquid chromatography on a chiral column of the configurational stereoisomers of difethialone (top) and of the dextrorotatory enantiomer of said hetero-stereoisomer of difethialone (bottom)—FIG. b1) represents a circular dichroism spectrum of the dextrorotatory enantiomer of said hetero-stereoisomer of difethialone—FIG. c1) is the proton NMR spectrum at 500 MHz of the dextrorotatory enantiomer of said hetero-stereoisomer of difethialone.
Figure 2:
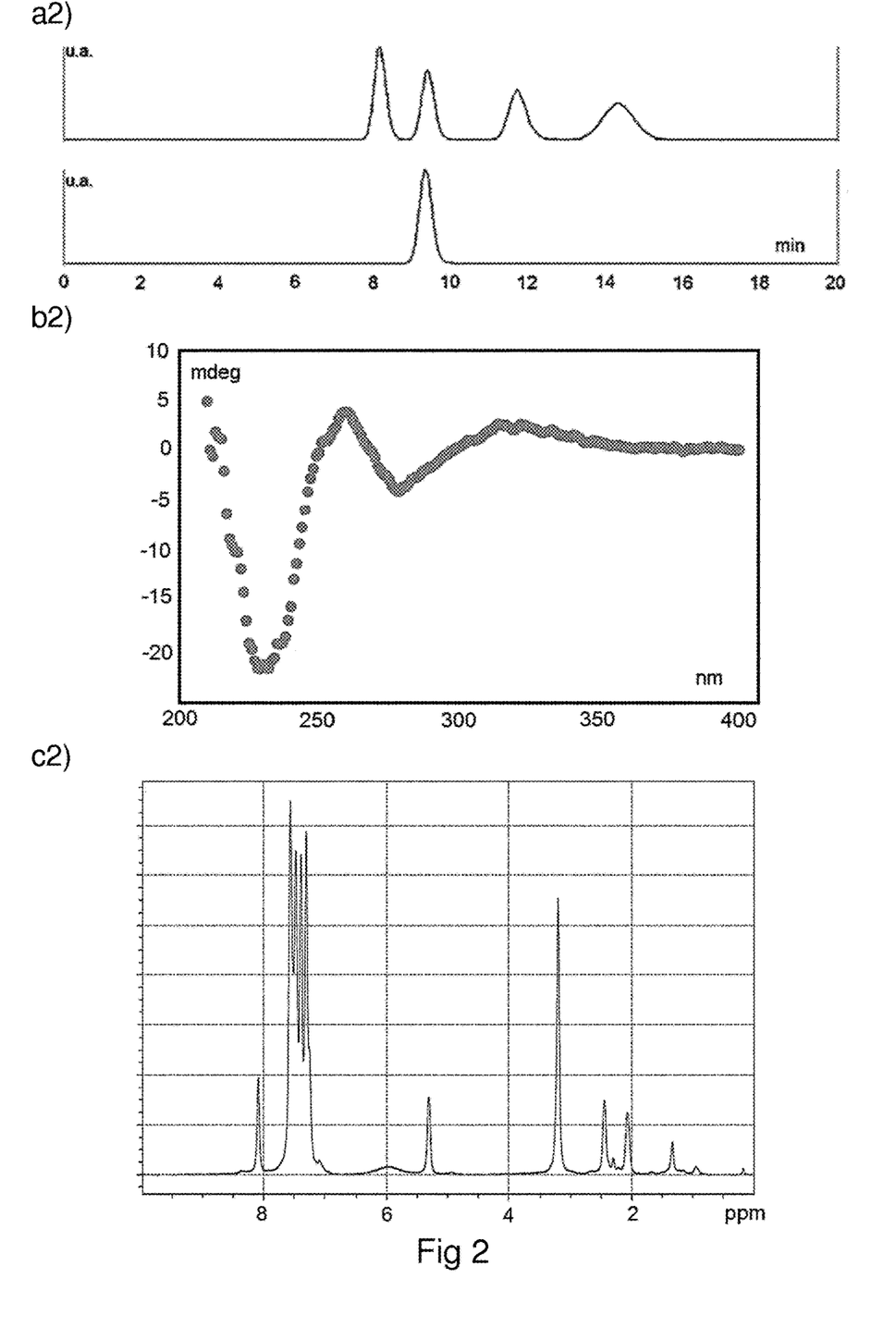
FIG. 2 relates to the laevorotatory enantiomer of said hetero-stereoisomer of difethialone—FIG. a2) represents an analysis by high-pressure liquid chromatography on a chiral column of the configurational stereoisomers of difethialone (top) and of the laevorotatory enantiomer of said hetero-stereoisomer of difethialone (bottom)—FIG. b2) represents a circular dichroism spectrum of the laevorotatory enantiomer of said hetero-stereoisomer of difethialone—FIG. c2) is the proton NMR spectrum at 500 MHz of the laevorotatory enantiomer of said hetero-stereoisomer of difethialone.
Figure 3:
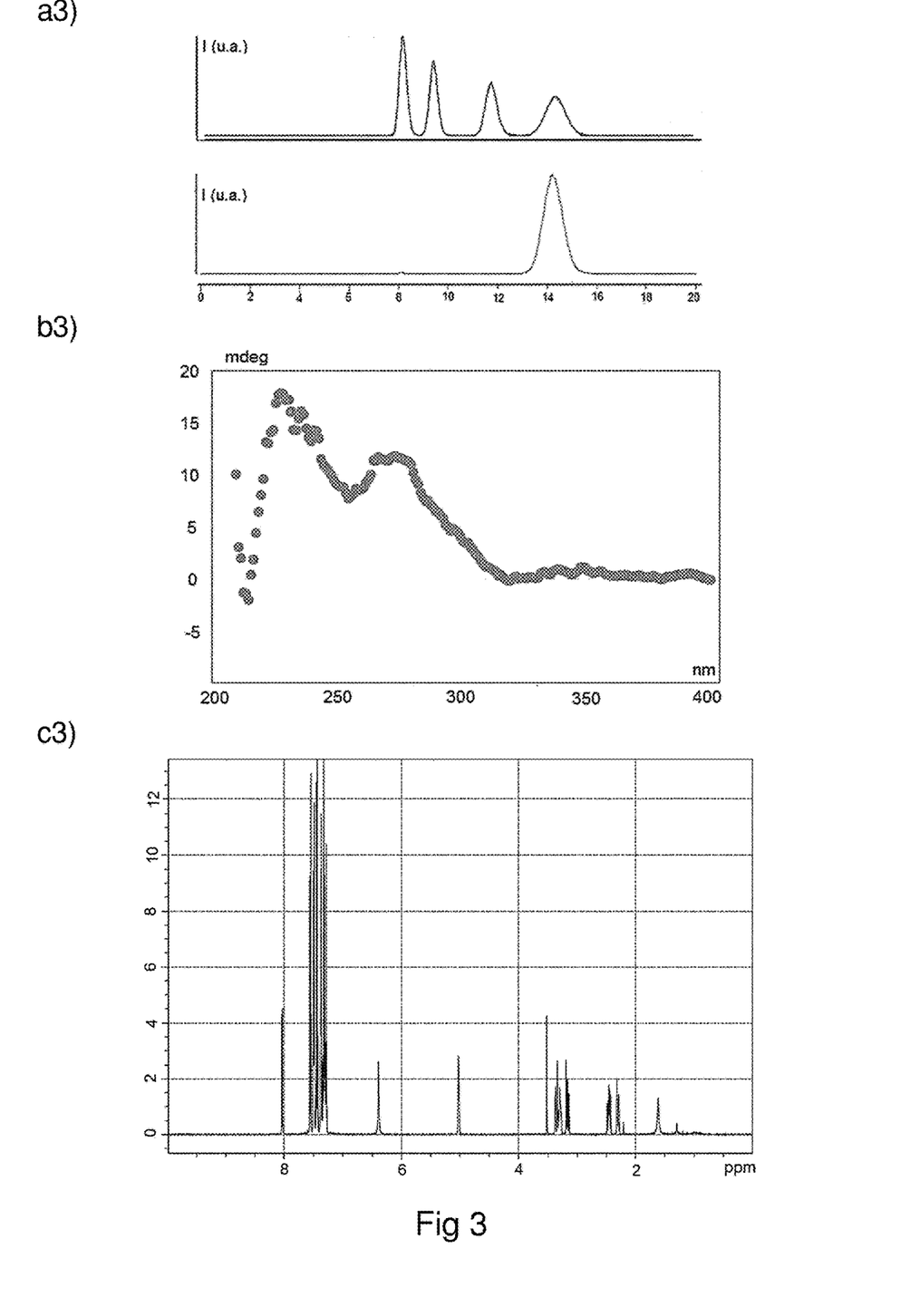
FIG. 3 relates to the dextrorotatory enantiomer of said homo-stereoisomer of difethialone—FIG. a3) represents an analysis by high-pressure liquid chromatography on a chiral column of the configurational stereoisomers of difethialone (top) and of the dextrorotatory enantiomer of said homo-stereoisomer of difethialone (bottom)—FIG. b3) represents a circular dichroism spectrum of the dextrorotatory enantiomer of said homo-stereoisomer of difethialone—FIG. c3) is the proton NMR spectrum at 500 MHz of the dextrorotatory enantiomer of said homo-stereoisomer of difethialone.
Figure 4:
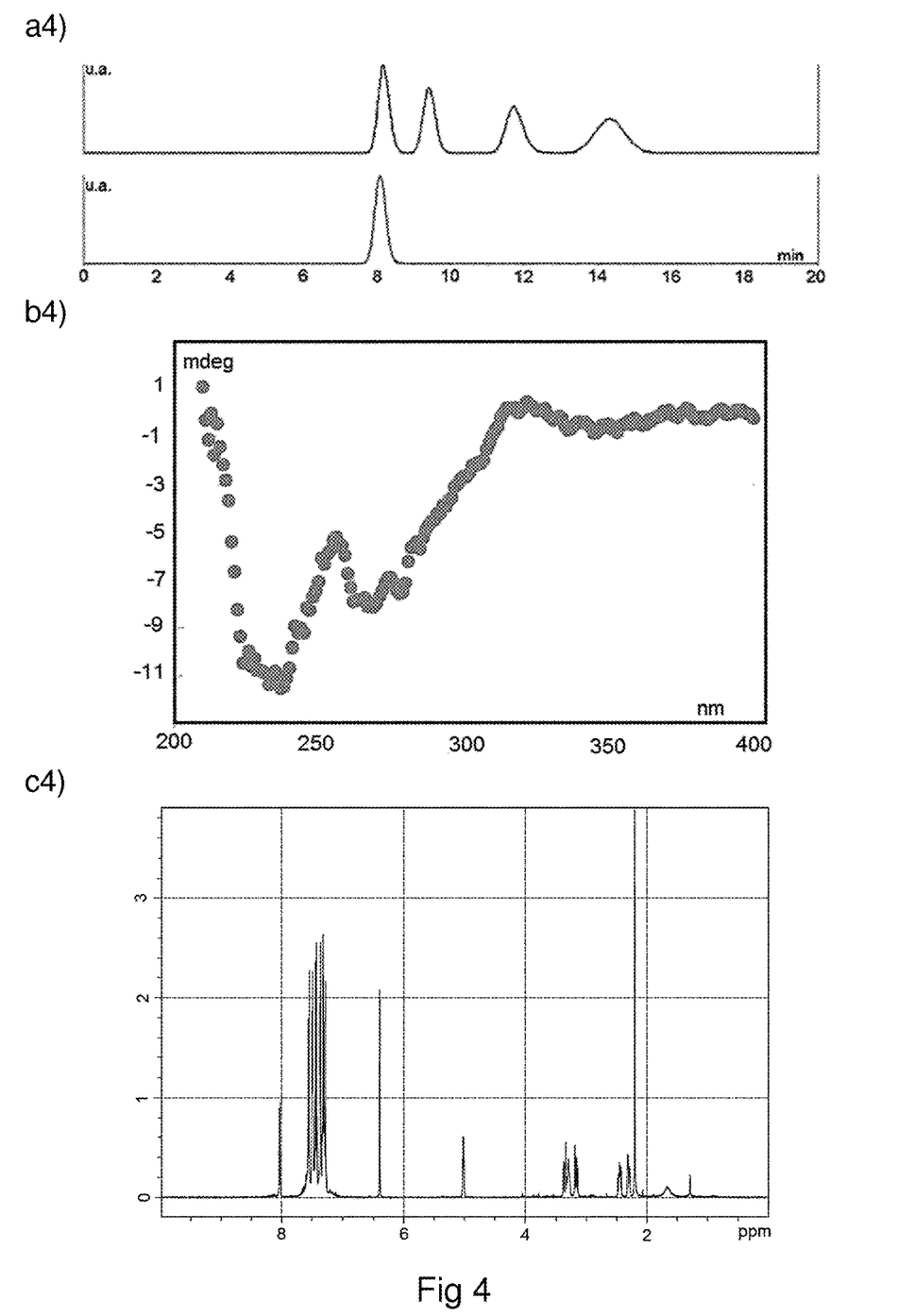
FIG. 4 relates to the laevorotatory enantiomer of said homo-stereoisomer of difethialone—FIG. a4) represents an analysis by high-pressure liquid chromatography on a chiral column of the configurational stereoisomers of difethialone (top) and of the laevorotatory enantiomer of said homo-stereoisomer of difethialone (bottom)—FIG. b4) represents a circular dichroism spectrum of the laevorotatory enantiomer of said homo-stereoisomer of difethialone—FIG. c4) is the proton NMR spectrum at 500 MHz of the laevorotatory enantiomer of said homo-stereoisomer of difethialone.

A.1. Identification of Said Homo-Stereoisomer of Difethialone and of Said Hetero-Stereoisomer of Difethialone The homo-stereoisomer of difethialone is identified by proton magnetic resonance ($^1$H-NMR) spectroscopy. The homo-stereoisomer of difethialone dissolved in $CDCl_3$ has a multiplet with a chemical shift (δ) of between 4.9 ppm and 5.1 ppm and corresponding to the proton borne by carbon 1 of the 1,2,3,4-tetrahydronaphthalene group of difethialone as illustrated in FIGS. c3) and c4).

The hetero-stereoisomer of difethialone is identified by its proton NMR spectrum acquired in $CDCl_3$, in which the chemical shift of the proton borne by carbon 1 of the 1,2,3,4-tetrahydronaphthalene group of said hetero-stereoisomer of difethialone is about 5.3 ppm.

A.2. Separation of the Laevorotatory and Dextrorotatory Enantiomers of Said Homo-Stereoisomer and of Said Hetero-Stereoisomer of Difethialone by High-Pressure Liquid Chromatography The inventors solved the complex and hitherto unresolved problem of separating the laevorotatory and dextrorotatory enantiomers of said hetero-stereoisomer of difethialone and of the laevorotatory and dextrorotatory enantiomers of said homo-stereoisomer of difethialone from a composition of difethialone that is predominantly in the form of said hetero-stereoisomer. They succeeded in separating the configurational stereoisomers of difethialone by high-pressure (high-performance) liquid chromatography on a LUX® Cellulose-3 chiral column (Phenomenex, Le Pecq, France) of dimensions 150×2 mm and comprising a chiral stationary phase constituted of porous particles of cellulose tris(4-methylbenzoate), with a particle size of 3 μm and a porosity of 1000 Å and using, as mobile phase, an eluent formed from a mixture of acetonitrile (A) and water comprising formic acid in a volume proportion of 0.1% in the water (B), with an AB volume ratio of 80/20. The flow rate of the mobile phase in the column is 0.25 mL/minute and the separation is performed at a temperature of 23.2° C. The solution containing the sample to be analysed is at a concentration of 1 μg of difethialone per millilitre of acetonitrile and is filtered through a regenerated cellulose membrane with a cut-off threshold of 0.2 μm. The volume injected onto the column is 1 μL.

In a process for separating the enantiomers of said homo-stereoisomer of difethialone, it is possible to detect said enantiomers leaving the high-pressure liquid chromatography column by tandem mass spectrometry (MS/MS) in negative electrospray ionization mode (ESI: ElectroSpray Ionization). The temperature of the nebulizer gas is 350° C. and its flow rate is 8 L/minute. The pressure of the nebulizer gas is brought to 2700 hPa. In particular, the MRM ("Multiple Reaction Monitoring") transitions m/z 537.1→151.0 and m/z 537.1→78.9, corresponding to the difethialone signals, are detected.

FIGS. a1), a2), a3) and a4) illustrate the separation of the configurational stereoisomers of difethialone.

Under these experimental conditions:
- the value of the retention time ($t_1$) for the laevorotatory enantiomer of said homo-stereoisomer is about 8.1 minutes as represented in FIG. a4);
- the value of the retention time ($t_2$) for the laevorotatory enantiomer of said hetero-stereoisomer of difethialone is about 9.4 minutes as represented in FIG. a2);
- the value of the retention time ($t_3$) for the dextrorotatory enantiomer of said hetero-stereoisomer of difethialone is about 11.7 minutes as represented in FIG. a1);
- the value of the retention time ($t_4$) for the dextrorotatory enantiomer of said homo-stereoisomer according to the invention is about 14.4 minutes as represented in FIG. a3);

such that the configurational stereoisomers of difethialone can be separated by high-pressure liquid chromatography on a chiral column. Thus, under these experimental conditions, the order of elution of the configurational stereoisomers of difethialone is such that $t_1<t_2<t_3<t_4$.

The inventors also observed that it is possible to perform preparative purification of each enantiomer of said homo-stereoisomer and of said hetero-stereoisomer of difethialone by chromatography on a preparative column of larger dimensions, especially a diameter of 20 mm, comprising a chiral stationary phase constituted of porous particles of cellulose tris(4-methylbenzoate) with a particle size of greater than 3 μm and under conditions similar to those described for the analytical chromatography.

It is possible to measure the amount of each configurational stereoisomer of difethialone by evaluating the area under the peak of the chromatogram corresponding to each configurational stereoisomer and, where appropriate, by comparing this area measurement with the areas obtained by analysis of samples comprising known amounts of configurational stereoisomers of difethialone.

B. STRUCTURAL CHARACTERIZATION

B.1. UV Spectroscopy

The UV spectrum of the dextrorotatory and laevorotatory enantiomers of said homo-stereoisomer and of said hetero-stereoisomer of difethialone dissolved in chloroform shows absorbance peaks centred at 238.2 nm and 259.5 nm.

B.2. Optical Rotation

The inventors characterized the dextrorotatory and laevorotatory enantiomers of said homo-stereoisomer and of said hetero-stereoisomer of difethialone in isolated form by means of their optical rotation (also known as the optical activity or circular birefringence), i.e. their ability to deviate the polarization plane of polarized light. Deviation of the polarization plane of polarized light clockwise facing the polarized light beam characterizes a dextrorotatory solution, and deviation of the polarization plane of polarized light anticlockwise facing the polarized light beam characterizes a laevorotatory solution and compound.

The optical rotation of a solution of a configurational stereoisomer of difethialone in chloroform is measured. The optical rotation of this solution is measured by means of a P 2000 digital polarimeter (JASCO, Bouguenais, France) operating with excitatory light with a wavelength of 589 nm. The mean optical rotation α obtained on two series of ten different measurements and the specific optical rotation at 25° C. $[\alpha]^{25°C}_{589\,nm}$ of each configurational stereoisomer of difethialone dissolved in chloroform, measured on the sodium D line (589 nm), are calculated. The results are given in table 1 below.

TABLE 1

| | Concentration, g/L | α | $[\alpha]^{25°C}_{589\,nm}$ |
|---|---|---|---|
| Dextrorotatory homo-stereoisomer | 11.6 | 2.308° | +19.9° |
| Laevorotatory homo-stereoisomer | 11.05 | −1.635° | −14.8° |
| Dextrorotatory hetero-stereoisomer | 6.3 | +0.573° | +9.1° |
| Laevorotatory hetero-stereoisomer | 6.95 | −0.904° | −13° |

B.3. Circular Dichroism

The circular dichroism spectrum of each isolated dextrorotatory and laevorotatory enantiomer of said homo-stereoisomer and of said hetero-stereoisomer of difethialone reflects the difference in absorbance ($\Delta A = A_L - A_R$) of the two waves of left circular polarization (LCP) of intensity $A_L$ and of right circular polarization (RCP) of intensity $A_R$. This makes it possible to distinguish the dextrorotatory and laevorotatory enantiomers of said homo-stereoisomer and of said hetero-stereoisomer of difethialone. This difference in absorbance of the two circularly polarized waves is measured in a J-815 circular dichroism spectrometer (JASCO, Bouguenais, France). 2 mL of solution of each configurational stereoisomer of difethialone in methanol at the concentration given in table 2 are prepared. The solution is transferred into a quartz spectrophotometer cuvette. The circular dichroism spectrum of the solution is measured at 25° C. between 163 nm and 900 nm.

TABLE 2

| | Concentration mg/mL | FIG. | Circular dichroism between 220 nm and 300 nm |
|---|---|---|---|
| Dextrorotatory homo-stereoisomer | 0.96 | 3b) | positive |
| Laevorotatory homo-stereoisomer | 0.81 | 4b) | negative |
| Dextrorotatory hetero-stereoisomer | 0.65 | 1b) | positive |
| Laevorotatory hetero-stereoisomer | 0.94 | 1c) | negative |

C. EXTRACTION OF DIFETHIALONE FROM THE LIVER OF RATS TREATED WITH DIFETHIALONE FOR THE PURPOSE OF ANALYSIS OF THE CONFIGURATIONAL STEREOISOMERS OF DIFETHIALONE

C.1. Homogenization of the Liver Sample

About 0.525 g (±0.025 g) of rat liver is weighed out accurately and placed in a 50 mL polypropylene tube. 10 mL of acetone are added and the suspension is homogenized using an Ultra-Turrax® homogenizer/disperser for a time of about 30 seconds. The homogenizer/disperser shaft is rinsed with hot water and then twice with 20 mL of acetone in a polypropylene tube. The homogenate is centrifuged for 5 minutes at a centrifugation speed of 3000 rpm (revolutions per minute). The supernatant is collected and transferred into a test tube. The sample is subjected to evaporation under a stream of nitrogen ($N_2$) at a temperature of 40° C. so as to form a dry extract.

C.2. Lipid Removal 1 mL of acetonitrile is added to the tube containing the dry extract so as to dissolve it. The acetonitrile solution is washed twice successively with 1 mL of hexane. The lipid-free extract is dried under a stream of nitrogen ($N_2$) at a temperature of 40° C. and is then taken up in 0.5 mL of methanol and dissolved by vortex stirring. 0.5 mL of ultra-pure (Milli-Q) water is then added. The sample is vortex-homogenized.

C.3. Solid-Phase Extraction (SPE) of Difethialone 1 mL of dichloromethane, then 1 mL of methanol, then 1 mL of ultra-pure (Milli-Q) water are passed through an Oasis HLB 1 cc cartridge (WAT094225, Waters). The lipid-free liver extract (1 mL of MeOH/Milli-Q $H_2O$) containing difethialone is then loaded onto the top of the cartridge so that the liver extract penetrates through the cartridge by gravity on contact with the solid phase. 1 mL of washing solution formed from methanol and ultra-pure water in a 90/10 volume proportion is then loaded onto the top of the cartridge. The cartridge is dried by suction under vacuum connected to the bottom of the cartridge. 1 mL of eluting solution formed from dichloromethane and methanol in a 90/10 volume proportion is then loaded onto the top of the cartridge and an eluate comprising difethialone is collected at the bottom of the cartridge. The solvent of the eluate is evaporated off under a stream of nitrogen ($N_2$) at a temperature of 40° C. The sample is taken up in 0.5 mL of acetonitrile and the acetonitrile solution containing difethialone is filtered through a 0.2 μm filter.

The composition is analysed by high-pressure liquid chromatography on a chiral column as described in point A2) above.

D. Study of the Hepatic Persistence of the Configurational Stereoisomers of Difethialone in Rats A solution of a mixture of homo-stereoisomer (DFN-Homo-SI) and of hetero-stereoisomer (DFN-Hetero-SI) of difethialone in a mixture of vegetable oil and 5% DMSO is administered by tube-feeding ("per os") to 8-week-old coumaphen-sensitive rats (male and female Rattus norvegicus) weighing about 200 g. The molar proportion of homo-stereoisomer is 40% and the molar proportion of hetero-stereoisomer is 60%. Each configurational stereoisomer of difethialone is formed from a racemic mixture of the two enantiomers of said corresponding configurational stereoisomer.

On D0, a tube-feeding solution is administered to each rat so that the amount of difethialone ingested by each rat is about 3.4 mg per kilogram of rat. To avoid haemorrhage, the rats are also treated daily by subcutaneous administration of a dose of vitamin K1 (as haemorrhage antidote) at a rate of 0.1 U per 200 g of live rat weight.

At 4 hours (H+4), 9 hours (H+9), 24 hours (H+24), 120 hours (H+120), 168 hours (H+168) and 216 hours (H+216) after tube-feeding, three male rats and three female rats anaesthetized beforehand with isoflurane are euthanized, the liver of the euthanized rats is removed, the difethialone is then extracted from the liver, the amount of each of the configurational stereoisomers of difethialone is assayed, the area under the peaks in the chromatogram obtained is measured and each configurational stereoisomer is quantified by comparison with a calibration curve. The following are assayed:
the dextrorotatory enantiomer of said homo-stereoisomer ("DFN-Homo-dextro");
the laevorotatory enantiomer of said homo-stereoisomer ("DFN-Homo-laevo");
the dextrorotatory enantiomer of said hetero-stereoisomer ("DFN-Hetero-dextro");
the laevorotatory enantiomer of said hetero-stereoisomer ("DFN-Hetero-laevo");
present in the liver of the tube-fed rats.

The results are given in table 3 below, in which each value is the mean of the contents measured on six rats (three male rats and three female rats) and expressed as nanograms of enantiomer per gram of liver (ng/g)).

TABLE 3

| Time after tube-feeding, hours | Hepatic content, ng/g Total difethialone | | | |
|---|---|---|---|---|
| | DFN-Homo-SI | | DFN-Hetero-SI | |
| | DFN-Homo-dextro | DFN-Homo-laevo | DFN-Hetero-dextro | DFN-Hetero-laevo |
| 4 | 4566 | 5692.5 | 10589.5 | 5380.5 |
| 9 | 4692.5 | 7141 | 12155.5 | 5869.5 |
| 24 | 1243.5 | 4403.5 | 8102 | 3613.5 |
| 48 | 720.5 | 3874 | 7974.5 | 2804 |
| 120 | 192.5 | 2087 | 5431.5 | 1211 |
| 168 | 129 | 878.5 | 3011 | 392.5 |
| 216 | 77.5 | 1224 | 4030.5 | 545 |

The dextrorotatory enantiomer of said hetero-stereoisomer of difethialone is the most persistent in the liver of target rodent pests.

Rodenticidal Bit Comprising a Mass Proportion of 14.7 ppm of Difethialone

A pasty rodenticidal bait according to the invention is prepared by dispersing an amount of dextrorotatory enantiomer of said homo-stereoisomer of difethialone in an edible excipient comprising vegetable fat and cereal flour. The measured proportion of difethialone relative to the bait is 14.7 ppm (14.7 mg of difethialone per kilogram of bait) and the proportion of dextrorotatory enantiomer of said homo-stereoisomer relative to the difethialone is 99.7%. The bait also comprises a mass proportion of 0.3% of laevorotatory enantiomer of said hetero-stereoisomer of difethialone relative to the difethialone. The rodenticidal bait according to the invention is substantially free of dextrorotatory enantiomer of said hetero-stereoisomer of difethialone.

On D0, ten coumaphen-sensitive Sprague-Dawley rats (five male and five female SD rats) are placed in individual cages with a rodenticide-free reference feed. On D3, each rat is weighed, and 50 g of rodenticidal bait as described above are then provided to each rat. This provision of 50 g of rodenticidal bait is renewed daily. The bait consumed by the rats is made up to 50 g of bait on D4, D5 and D6. Starting from D7, the residual rodenticidal baits are removed and rodenticide-free feed is provided to all the rats. The rats are monitored for 3 weeks.

The mean amounts of bait consumed daily by a rat at D4, D5, D6 and D7 expressed in grams per day are given in table 4 below.

TABLE 4

| Bait consumed, g | Mean | Standard deviation |
|---|---|---|
| D4 | 17.8 | 5.7 |
| D5 | 16.0 | 4.7 |
| D6 | 14.2 | 4.1 |
| D7 | 9.4 | 3.8 |

It should be noted that no rat consumed a daily amount of bait of less than 1 g/day. All the rats (100%) die between D9 and D10. The mortality is 100% on D10.

The bait containing a 14.7 ppm dose of difethialone (including 99.7% of dextrorotatory enantiomer of said homo-stereoisomer of difethialone) makes it possible to obtain a mortality rate of 100% while minimizing the risks of secondary intoxication of animals—especially birds—which prey or carrion-feed on weakened target rodent pests that have consumed a rodenticidal bait.

It goes without saying that the invention may be the subject of numerous implementation variants and applications. In particular, a composition, a rodenticidal bait and a process for controlling target rodent pests are subject to an infinite number of variants both in the formulation of the bait and in the embodiments of the process.

The invention claimed is:

1. Rodenticidal bait comprising:
   Difethialone; and
   at least one excipient that is edible for target rodent pests, wherein said difethialone has a configurational stereoisomer of difethialone, named hetero-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have different absolute configurations, the rodenticidal bait comprising an amount of dextrorotatory enantiomer of said hetero-stereoisomer such that the ratio of this amount to the amount of difethialone in the rodenticidal bait is less than 10%; the amount of the dextrorotatory enantiomer of said hetero-stereoisomer of difethialone in the rodenticidal bait being different from the amount of laevorotatory enantiomer of said hetero-stereoisomer of difethialone in the rodenticidal bait.

2. Rodenticidal bait according to claim 1, further comprising a configurational stereoisomer of difethialone, named homo-stereoisomer, the formula of which is 3-(4'-bromobiphenyl-4-yl)-1-(4-hydroxythiocoumarin-3-yl)-1,2,3,4-tetrahydronaphthalene, in which carbons 1 and 3 of the 1,2,3,4-tetrahydronaphthalene group have the same absolute configuration, the rodenticidal bait comprising an amount of a laevorotatory enantiomer of said homo-stereoisomer of difethialone such that the ratio of the amount of laevorotatory enantiomer of said homo-stereoisomer of difethialone to the total amount of difethialone in the rodenticidal bait is less than 10%.

3. Rodenticidal bait according to claim 1, further comprising an amount of a laevorotatory enantiomer of said hetero-stereoisomer of difethialone such that the ratio of the amount of the laevorotatory enantiomer of said hetero-stereoisomer of difethialone in the rodenticidal bait to the total amount of difethialone in the rodenticidal bait is less than 10%.

4. Composition according to claim 1, further comprising an amount of the dextrorotatory enantiomer of said homo-stereoisomer of difethialone such that the ratio of this amount to the total amount of difethialone in the composition is between 10% and 100%.

5. Rodenticidal bait according to claim 1, wherein the edible excipient comprises at least one food chosen from the group formed from cereal seeds, cereal seed meals, cereal seed flours, cereal seed flakes, cereal bran and non-cereal seeds.

6. Rodenticidal bait according to claim 1, further comprising a mass amount of difethialone such that the ratio of this mass amount of difethialone to the mass amount of rodenticidal bait is less than 200 ppm.

7. Rodenticidal bait according to claim 2, further comprising an amount of a laevorotatory enantiomer of said hetero-stereoisomer of difethialone such that the ratio of the amount of the laevorotatory enantiomer of said hetero-stereoisomer of difethialone in the rodenticidal bait to the total amount of difethialone in the rodenticidal bait is less than 10%.

8. Composition according to claim 2, further comprising an amount of the dextrorotatory enantiomer of said homo-stereoisomer of difethialone such that the ratio of this amount to the total amount of difethialone in the composition is between 10% and 100%.

9. Composition according to claim 3, further comprising an amount of the dextrorotatory enantiomer of said homo-stereoisomer of difethialone such that the ratio of this amount to the total amount of difethialone in the composition is between 10% and 100%.

10. Rodenticidal bait according to claim 2, wherein the edible excipient comprises at least one food chosen from the group formed from cereal seeds, cereal seed meals, cereal seed flours, cereal seed flakes, cereal bran and non-cereal seeds.

11. Rodenticidal bait according to claim 3, wherein the edible excipient comprises at least one food chosen from the group formed from cereal seeds, cereal seed meals, cereal seed flours, cereal seed flakes, cereal bran and non-cereal seeds.

12. Rodenticidal bait according to claim 4, wherein the edible excipient comprises at least one food chosen from the group formed from cereal seeds, cereal seed meals, cereal seed flours, cereal seed flakes, cereal bran and non-cereal seeds.

13. Rodenticidal bait according to claim 2, further comprising a mass amount of difethialone such that the ratio of this mass amount of difethialone to the mass amount of rodenticidal bait is less than 200 ppm.

14. Rodenticidal bait according to claim 3, further comprising a mass amount of difethialone such that the ratio of this mass amount of difethialone to the mass amount of rodenticidal bait is less than 200 ppm.

15. Rodenticidal bait according to claim 4, further comprising a mass amount of difethialone such that the ratio of this mass amount of difethialone to the mass amount of rodenticidal bait is less than 200 ppm.

16. Rodenticidal bait according to claim 5, further comprising a mass amount of difethialone such that the ratio of this mass amount of difethialone to the mass amount of rodenticidal bait is less than 200 ppm.

17. Composition according to claim 7, further comprising an amount of the dextrorotatory enantiomer of said homo-stereoisomer of difethialone such that the ratio of this amount to the total amount of difethialone in the composition is between 10% and 100%.

18. Rodenticidal bait according to claim 7, wherein the edible excipient comprises at least one food chosen from the group formed from cereal seeds, cereal seed meals, cereal seed flours, cereal seed flakes, cereal bran and non-cereal seeds.

19. Rodenticidal bait according to claim 8, wherein the edible excipient comprises at least one food chosen from the group formed from cereal seeds, cereal seed meals, cereal seed flours, cereal seed flakes, cereal bran and non-cereal seeds.

20. Rodenticidal bait according to claim 9, wherein the edible excipient comprises at least one food chosen from the group formed from cereal seeds, cereal seed meals, cereal seed flours, cereal seed flakes, cereal bran and non-cereal seeds.

* * * * *